United States Patent [19]

Nygren et al.

[11] Patent Number: 4,673,584

[45] Date of Patent: Jun. 16, 1987

[54] PROCESS FOR PROVIDING ARTICLES WITH A BIOCOMPATIBLE SURFACE LAYER

[75] Inventors: Bo H. Nygren, Billdal; Johan E. Stenberg, Gothenburg, both of Sweden

[73] Assignee: Astra Meditec AB, Sweden

[21] Appl. No.: 836,318

[22] Filed: Mar. 5, 1986

Related U.S. Application Data

[62] Division of Ser. No. 576,377, Jan. 13, 1984, Pat. No. 4,588,624.

[30] Foreign Application Priority Data

May 14, 1982 [SE] Sweden ................................. 8203029

[51] Int. Cl.$^4$ ............................................. A01N 1/02
[52] U.S. Cl. .................................. 427/2; 427/407.1; 427/407.2; 427/410; 427/412.1
[58] Field of Search ............... 427/2, 386, 387, 389.7, 427/407.1, 409, 410, 407.2, 412.1

[56] References Cited

U.S. PATENT DOCUMENTS

| | | | |
|---|---|---|---|
| 3,434,869 | 3/1969 | Davidson | 117/94 |
| 3,457,098 | 7/1969 | Leininger et al. | 427/386 X |
| 3,683,926 | 8/1972 | Suzuki | 128/334 R |
| 3,755,218 | 8/1973 | Yen et al. | 260/9 |
| 3,766,104 | 10/1973 | Bonin et al. | 260/9 |
| 3,810,781 | 5/1974 | Eriksson et al. | 260/47 A |
| 3,846,353 | 11/1974 | Grotta | 260/9 |
| 3,976,819 | 8/1976 | Mori et al. | 427/407.2 X |
| 4,027,676 | 6/1977 | Mattei | 128/335.5 |
| 4,069,368 | 1/1978 | Devak et al. | 427/386 X |
| 4,118,845 | 10/1978 | Eriksson et al. | 424/183 |
| 4,199,649 | 4/1980 | Yundt | 427/407.2 X |
| 4,215,165 | 7/1980 | Gras et al. | 427/407.2 X |
| 4,282,287 | 8/1981 | Giese | 427/2 |
| 4,301,115 | 11/1981 | Rapkin et al. | 427/2 X |
| 4,304,802 | 12/1981 | Mosse et al. | 427/386 |
| 4,363,634 | 12/1982 | Schall, Jr. | |
| 4,588,624 | 5/1986 | Nygren et al. | 428/36 |

FOREIGN PATENT DOCUMENTS

| | | |
|---|---|---|
| 0051354 | 5/1982 | European Pat. Off. |
| 2154542 | 5/1972 | Fed. Rep. of Germany |
| 2034413 | 6/1972 | Fed. Rep. of Germany |
| 2206608 | 8/1972 | Fed. Rep. of Germany |
| 0365710 | 4/1974 | Sweden |
| 0400173 | 3/1978 | Sweden |
| 0084463 | 10/1979 | Sweden |
| 1319007 | 5/1973 | United Kingdom |
| 1357452 | 6/1974 | United Kingdom |
| 1483014 | 8/1977 | United Kingdom |
| 1498981 | 1/1978 | United Kingdom |
| 2033232 | 5/1980 | United Kingdom |
| 2041377 | 9/1980 | United Kingdom |

OTHER PUBLICATIONS

Chemical Abstract, vol. 83, No. 10, p. 369, No. 84823v.

*Primary Examiner*—Thurman K. Page
*Attorney, Agent, or Firm*—Brumbaugh, Graves, Donohue & Raymond

[57] ABSTRACT

A process for providing a surface of glass, silicon, aluminum or silicone rubber of an article useful within medicine with a biocompatible surface layer. Said surface is reacted (after oxidation when required) with a silane containing at least one epoxy group and the surface thus treated is then reacted with a polysaccharide containing at least one hydroxyl group. The invention also relates to an article exhibiting a biocompatible surface layer of a polysaccharide containing at least one hydroxyl group, which polysaccharide is covalently bound to a surface of glass, silicon, aluminum or silicone rubber of the article by means of a silane.

5 Claims, No Drawings

PROCESS FOR PROVIDING ARTICLES WITH A BIOCOMPATIBLE SURFACE LAYER

This application is a division of application Ser. No. 576,377, filed on Jan. 13, 1984 and now U.S. Pat. No. 4,588,624.

The present invention relates to articles exhibiting a biocompatible surface layer and a process for providing articles with such a surface layer. More particularly, the invention relates to articles exhibiting at least one surface of glass, silicon, aluminum or silicone rubber coated with a biocompatible surface layer and a process for providing articles exhibiting at least one surface of glass, silicon, aluminum or silicone rubber with a biocompatible surface layer.

The object of the present invention is to provide articles useful within medicine with a biocompatible surface layer. This means, for instance for articles intended for use in contact with blood, that the article which is alien to the blood is treated in such a way that it does not induce coagulation or formation of thromboses.

Prior art techniques to provide articles useful in medicine with a biocompatible surface layer often comprise an alteration in the surface energy of the material. An improvement in the properties of various materials has been obtained by modifying the surface layers either to a more hydrophobic character or to a more hydrophilic character. Hydrophobization of the surface layer, for instance by the methylization of a glass surface, results in a decrease in the effectiveness of the surface activated coagulation system of the blood. However, proteins such as fibrinogen are bound comparatively firmly to such surfaces and to this protein layer certain cells, the thrombocytes, can be bound and activated whereafter coagulation is started even though it proceeds slowly. Hydrophilic surfaces, e.g. hydrolysed nylon or oxidized aluminium, have presented reduced binding of cells but the surface activated coagulation system is not prevented at these surfaces. The use of these surfaces in contact with blood thus implies the addition of anticoagulants, for instance heparin, to the blood.

Another prior art surface treatment technique for preventing coagulation comprises binding of anticoagulants into the surface layer. Heparin has primarily been used with this technique. Heparin is a hexoseaminehexuronic acid polysaccharide which is sulphatized and has acid properties, i.e. heparin is an organic acid. According to DE-A-21 54 542 articles of an organic thermoplastic resin are first impregnated with an aminosilane coupling agent and the articles thus treated are then reacted with an acid solution of a heparin salt to the binding of heparin in the surface layer by means of ionic bonds. Surfaces thus treated with heparin have proved to reduce the coagulation reaction. A considerable disadvantage of these surfaces, however, is that the heparin treatment does not prevent the adherence of thrombocytes, which is a great problem in, for instance, heart-lung machines.

It is also known that water-binding gels, for instance polyhydroxyalkyl methacrylate, reduce the adsorption of proteins and present a low adhesiveness to cells (Hoffman et al. Ann. New York Acad. Sci., Vol. 283 (1977) 372). These properties are considered to be due to the fact that gels containing water give a low surface energy in the interface to the blood. The prior art technique for manufacturing of water-binding gels, however, is impaired by disadvantages such as complicated preparation technique and incomplete polymerisation, which results in leakage of toxic monomers. A gel-like mixture of saccharose and glycose included in a matrix of the polysaccharide dextran or dextrin is used in accordance with previously known technique as a tube for the connection of blood-vessels. This mixture should have the effect that no toxicity to the patient occurs and that the implantate is dissolved in the blood after some time. It is known that the neutral polysaccharide dextran is miscible with blood without provoking any coagulation reaction.

The present invention combines the property of water-binding gels with the low toxicity of polysaccharides at the same time as it affords a technique for the surface treatment of materials important for medical technology, such as glass, silicon, aluminum and silicon rubber. (The term "glass" as used here and in the claims is intended to include also quartz.)

The article according to the invention which exhibits at least one surface of glass, silicon, aluminum or silicone rubber coated with a biocompatible surface layer, is characterized in that the biocompatible surface layer consists of a polysaccharide containing at least one hydroxyl group, which polysaccharide is covalently bound to said surface of glass, silicon, aluminum or silicone rubber of the article by means of a silane.

The process according to the invention for providing articles exhibiting at least one surface of glass, silicon, aluminum or silicone rubber with a biocompatible surface layer is characterized in that said surface of the article, after oxidation thereof when required, is reacted with a silane containing at least one epoxy group and that the surface thus treated is reacted with a polysaccharide containing at least one hydroxyl group.

The silane can be an alkoxy silane $(R-Si(OCH_3)_3)$ or a chlorosilane $(R-SiCl_3)$, in which formulas $R-$ represents an epoxy group

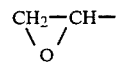

which is coupled to the silicone atom via a hydrocarbon chain (in most cases propyl).

The hydrolysed silane forms an active silane $(R-Si(OH)_3)$, which reacts with inorganic compounds, which exhibit hydroxyl groups at their surface. Examples of such materials are glass, silicon, oxidized aluminum and oxidized silicone rubber, which materials after hydration obtain hydroxyl groups in the surface layer. The reaction between the inorganic substance of the surface layer and the silanol is prior art technique (Dow Corning Product Bulletin 23-181 C 1980) and this reaction proceeds in the following way:

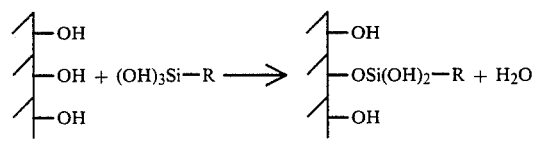

whereafter the silanol is polymerized laterally

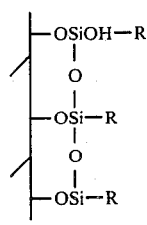

The final result is a surface which is coated with the functional group of the silanol. The polysaccharide can then in a second step be coupled to the surface. In the following example the reaction between the polysaccharide P and a silanised surface is described, the functional group of R being an epoxy group as stated above. The polysaccharide P is bound to the epoxy group via the hydroxyl groups of the polysaccharide according to the reaction

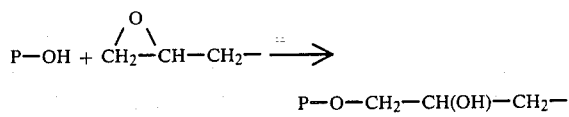

Optimum conditions for this reaction have been investigated previously (vide Sundberg and Porath, J. Chromatogr. 90 (1974) 87).

Acccording to one aspect of the invention the polysaccharide P may be neutral. According to another aspect of the invention the polysaccharide can be a polysaccharide occurring in nature, such as dextran, or a synthetic polysaccharide prepared, for instance, by polymerization of mono- or disaccharides by means of chemical reactants such as epichlorohydrin.

The dextran can be ethyl-, hydroxyethyl- or 2-hydroxypropylether of dextran or dextran glycerol glycoside or hydrodextran (i.e. dextran, the reducing end groups of which are reduced to alcohol groups) or hydroxyl group-containing hydrophilic derivatives of dextran or partially degraded dextran.

After the binding to the surface layer the polysaccharide can be polymerized further so that a thicker layer is obtained. This polymerization has been described in SE-A-169 293.

The treated surface proves biologically inert and surfaces treated in this way give reduced absorption of proteins, adherence, of cells and coagulation. The process according to the present invention can be applied within many different fields. Thus in heart-lung machines there are used many details which are made of aluminum. The surfaces coming into contact with blood are easily oxidized to aluminium oxide in order to be subsequently treated according to the process according to the invention. This process can be applied to other mechanical details which are intended to be in contact with blood, e.g. in apparatuses for dialysis.

Catheters of silicone rubber can also be treated by means of the process according to the invention. In that case the silicone rubber must first be made reactive by oxidizing a thin surface layer. This is effected by means of an etching process which implies that the surface layer is oxidized in an oxygen plasma at a low pressure. This process does not result in any impairment of the properties of the material. After the etching the surface proves hydrophilic and reactive against silanes and it can be treated by means of the process according to the invention.

The invention may also be applied in other connections, for instance for the treatment of articles of aluminum, glass or silicone rubber for sampling and/or storage of blood.

The invention will be illustrated by the following working Examples but is not limited thereto and hence modifications are of course conceivable within the limits of the claims.

EXAMPLE 1

(a) A piece of silicone rubber having the size 4×4 centimeters and a thickness of 2 millimeters was treated with a 10% (v/v) solution of conventional detergents for manual dishwashing and was subsequently rinsed thoroughly with running distilled water. The piece was then etched in an oxygen plasma, 300 millibar $O_2$, 100 W, for 3 minutes and then immediately immersed in water.

(b) The piece of silicone rubber was picked up from the water and the surfaces thereof were blown so that visible water disappeared whereafter it was immediately immersed in a 5% (w/v) solution of 3-glycidoxypropyl trimethoxysilane (Epoxysilane) in propanol for 10 minutes. The piece of silicone rubber was completely covered by the solution.

Then the piece was dried in an oven at 60° C. to apparent dryness, washed in distilled water and blown dry. The surface was now hydrophobic.

(c) The piece treated according to (b) was immersed into a 20% (w/v) solution of dextran having an average molecular weight ($\overline{M}_w$) of 2,000,000 in distilled water and was allowed to react for 20 h at room temperature. The surface was now hydrophilic.

EXAMPLE 2

(a) A cover glass was treated with dichromatesulphuric acid and thoroughly rinsed with running distilled water.

(b) The cover glass treated according to (a) was reacted with 3-glycidoxypropyl trimethoxysilane according to Example 1(b) above.

(c) The cover glass treated according to (b) was immersed into a 40% (w/v) solution of dextran having an average molecular weight ($\overline{M}_w$) of 200,000 in distilled water and was allowed to react for 20 h at room temperature. The obtained surface was hydrophilic. The thickness of the applied layer was 4 nanometers as determined by ellipsometry.

EXAMPLE 3

(a) A piece of aluminum having the size 2×4 centimeters and a thickness of about 1 millimeter was treated with a 10% (v/v) solution of conventional detergents for manual dishwashing and was subsequently rinsed with distilled water over night.

(b) The piece of aluminum treated according to (a) was reacted with 3-glycidoxypropyl trimethoxysilane using the procedure described in Example 1 (b) above.

(c) The piece of aluminum treated according to (b) was immersed into a 20% (w/v) solution of dextran having an average molecular weight ($\overline{M}_w$) of 200,000 in distilled water and was allowed to react for 20 h at room temperature. The obtained surface was hydrophilic.

EXAMPLE A

Biocompatibility test

Cover glasses treated analogously to Example 2 (except that a 20% (w/v) solution of a dextran having an average molecular weight ($\overline{M}_w$) of 2,000,000 was used in step (c) were used as an article according to the invention in this experiment. The thickness of the dextran layer was 5 nanometers. The dextran-coated cover glasses were wetted and preincubated in a humidified chamber at 37° C. followed by the experimental incubation with blood. Incubation was performed for 10 min at 37° C. with untreated rat blood obtained by cutting off ether anesthesized rats. Untreated cover glasses and methylized glasses (Elwing, H. and Stenberg, M; J. Immunol. Meth. 44 (1981) 343–345) were used as positive controls of clot formation and platelet adhesion. After incubation, the clots were cut in two halves with a razor blade. One half was gently removed and the glasses were rinsed in phosphate-buffered saline (0.05M phosphate buffer pH 7.4) for 5–10 sec with a flow of 1.5–2 lit/min. Fixation was performed in 1.15M cacodylate buffer pH 7.4 with 3% glutaraldehyde for 2 h, followed by dehydration in ethanol and drying in air or in a critical point drier. Specimens were coated with gold and examined in a JEOL 100 cx Scanning Electron microscope at an accelerating voltage of 20 kV.

RESULTS

At the end of incubation time, the blood samples had clotted against untreated glass and against methylized glass. Blood incubated on dextran-coated glass according to the invention showed clumps of clots whereas the bulk stayed fluid. The clumps did not adhere to the surface, and seemed to be induced in the blood/air interface. When examined in the scanning electron microscope, the interface between untreated glass and the thrombus was found to consist of fibrin-anchored erythrocytes and platelets. Hydrophobic, methylized glass on the other hand, induced an initial layer of adhering, activated platelets onto which other blood cells adhered. Fibrin threads were sparcely found close to the surface, but could be seen within the thrombus. Dextran-coated glass surfaces according to the invention failed to induced thrombus formation. When examined in the SEM, more than 90% of the surface area was free of cells and fibrin. Scattered solitary erythrocytes and platelets could be seen. The round appearance of the platelets on the dextran-coated surface was in sharp contrast to the more extended and flat shape of the platelets seen on the hydrophobic surface, indicating that the round cells were adhering to but not activated by the dextran-coated surface.

What is claimed is:

1. A process for providing articles exhibiting at least one surface of glass, silicon, aluminum or silicone rubber with a biocompatible surface layer, wherein said surface of the article, after oxidation thereof when said article is silicone rubber, is reacted with a silane containing at least one epoxy group and wherein the surface thus treated is reacted with a polysaccharide containing at least one hydroxyl group.

2. A process according to claim 1, wherein a neutral polysaccharide is used as said saccharide.

3. A process according to claim 2, wherein dextran is used as said neutral polysaccharide.

4. A process according to claim 1 wherein the silane is an alkoxysilane of the formula R-Si(alkoxy)$_3$, or a chlorosilane, of the formula R-SiCl$_3$ and wherein R represents an epoxy group

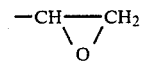

which is coupled to the silicone atom by means of a hydrocarbon chain.

5. A process according to claim 1 wherein the silane is 3-glycidoxypropyl trimethoxy silane.

* * * * *